United States Patent
Yu

(10) Patent No.: US 7,402,409 B2
(45) Date of Patent: Jul. 22, 2008

(54) CELL FUSION METHOD

(75) Inventor: Guo-Liang Yu, Berkeley, CA (US)

(73) Assignee: Epitomics, Inc., Burlingame, CA (US)

( * ) Notice: Subject to any disclaimer, the term of this patent is extended or adjusted under 35 U.S.C. 154(b) by 730 days.

(21) Appl. No.: 10/350,841

(22) Filed: Jan. 23, 2003

(65) Prior Publication Data

US 2004/0148643 A1 Jul. 29, 2004

(51) Int. Cl.
  C12P 21/08 (2006.01)
  C12N 5/06 (2006.01)
  C12N 5/16 (2006.01)
  C07H 21/04 (2006.01)

(52) U.S. Cl. .................. 435/69.1; 435/70.21; 435/326; 435/449; 530/387.1; 530/387.3; 530/388.1; 536/23.5; 536/23.53

(58) Field of Classification Search ........................ None
  See application file for complete search history.

(56) References Cited

U.S. PATENT DOCUMENTS

| | | | |
|---|---|---|---|
| 5,675,063 A | 10/1997 | Knight | |
| 6,197,578 B1 | 3/2001 | Berger et al. | |
| 6,420,140 B1 | 7/2002 | Hori et al. | |
| 6,451,598 B1 | 9/2002 | Goldsmith et al. | |

OTHER PUBLICATIONS

Jones et al, Advanced Drug Delivery Reviews 1998, pp. 153-170.*
Spieker-Polet et al, PNAS, 1995, vol. 92, pp. 9348-9352.*
Westerwoudt, Journal of Immunological Methods, 1985, vol. 77, pp. 181-196.*
Hori et al, Journal of Immunology, 1998, vol. 160, pp. 180-188).*
Tomita et al (Journal of Immunological Methods, 2001, vol. 251, pp. 31-43).*
Conrad and Lo (Methods in Enzymology, 1990, vol. 184, pp. 641-653).*
Lo et al (Nature, 1984, vol. 310, pp. 792-793).*
Holler et al (Blood, 1998, vol. 86, pp. 890-899).*
Wojchowski et al (Journal of Immunological Methods, 1986, vol. 90, pp. 173-177).*
Goto et al (Blood, 1994, vol. 84, pp. 1922-1930).*
Ahmad et al., Fusogenic Potential of Prokaryotic Membrane Lipids, Eur. J. Biochem., 2001, 268:5667-75.
Bates et al., A Receptor for Subgroup A Rous Sarcoma Virus is Related to the Low Density Lipoprotein Receiptor, Cell, 1993, 74:1043-1051.
Dzau et al., Fusigenic Viral Liposome for Gene Therapy in Cardiovascular Diseases, Proc Natl. Acad. Sci., 1996, 93:11421-5.
Dutch et al., Virus Membrane Fusion Proteins: Biological Machines That Undergo a Metamorphosis, Bioscience Reports, 2000, 20(6): 597-612.
Eckert et al., Mechanisms of Viral Membrane Fusion and its Inhibition, Annu. Rev. Biochem., 2001, 70:777-810.
Garzelli et al., Human Monoclonal Antibody to Purified Protein Derivative of Tubercullin Produced by Hybrids Constructed with Epstein-Barr Virus-Transformed B Lymphocytes and Mouse Myeloma Cells, Eur. J. Immunol., 1986, 16:584-7.
Gilbert et al., Receptor-Induced Conformational Changes in the Subgroup a Avian Leukosis and Sarcoma Virus Envelope Glycoprotein, J. Virol., 1995, 69(12):7410-15.
Hernandez et al., Virus-Cell and Cell-Cell Fusion, Annu. Rev. Cell. Dev. Biol., 1996, 12:627-61.
Hughson et al., Molecular Mechanisms of Protein-Mediated Membrane Fusion, Curr. Opinion in Struc. Biol., 1995, 5:507-513.
Kudo et al., New Strategies to Establish Human Monoclonal Antibodies, 1992, J. Exp. Med., 168:323-7.
Martin et al., Common Properties of Fusion Peptides From Diverse Systems, 2000, Bioscience Reports, 20(6): 483-500.
Nagata et al., Preferential Generation of Monoclonal IGG-Producing Hybridomas by Use of Vesicular Stomatitis Virus-Mediated Cell Fusion, 1991, Hybridoma, 10:369-78.
Shirahata et al., Cell Hybridization, Hybridomas, and Human Hybridomas, Methods Cell Biol., 1998, 57:111-45.
White et al., Membrane Fusion, Science, 1992, 258:917-924.

* cited by examiner

*Primary Examiner*—Karen A. Canella
(74) *Attorney, Agent, or Firm*—James S. Keddie

(57) ABSTRACT

The invention provides methods for fusing a first cell with a second cell to form a hybrid cell. The methods involve incubating a first parental cell producing a first partner of a fusogenic binding partner pair on its surface with a second parental cell producing a second partner of the fusogenic binding partner pair on its surface. In certain embodiments, the parental cells are incubated with a known fusogen such as polyethylene glycol and the fusogenic binding partner pair increases the rate of cell fusion. In many embodiments, the first cell is an antibody producing cell, the second cell is an immortal cell, and the hybrid cell is a hybridoma cell that produces a monoclonal antibody. Also provided by the invention are methods for producing hybridoma cells, and methods for screening those cells for production of a monoclonal antibody of interest. The invention further provides systems and kits for carrying out the subject methods. The subject methods, systems, and kits find use in a variety of different industrial, medical and research applications.

22 Claims, 2 Drawing Sheets

CELL FUSION METHOD

INTRODUCTION

1. Field of the Invention

The invention relates to methods for fusing two cells to make a hybrid cell. The methods find use in the production of hybridoma cells for producing monoclonal antibodies.

2. Background of the Invention

Monoclonal antibodies have been available for over 25 years and have revolutionalized biomedical research, especially in the areas of disease diagnosis and the treatment of infection and diseases.

The conventional method for the production of monoclonal antibodies involves hybridomas (Köhler & Milstein, Nature 256:495-7, 1975). In this method, splenic or lymphocyte cells from a mammal which has been injected with antigen are fused with a tumor cell line, thus producing hybrid cells. These hybrid cells, or "hybridomas", are both immortal and capable of producing the genetically coded antibody of a B cell. To select a hybridoma producing a single antibody, the hybridomas made by cell fusion are segregated by selection, dilution, and regrowth until a single genetically pure antibody-expressing cell line is selected. Because hybridomas produce homogeneous antibodies against a desired antigen, they are called "monoclonal" antibodies. Hybridoma technology has primarily been focused on the fusion of murine cells, however human-human hybridomas, human-murine hybridomas, rabbit-rabbit hybridomas and other xenogenic hybrid combinations have been made as well.

Monoclonal antibodies produced by hybridomas, while clearly preferable to polyclonal antibodies because of their specificity and affinity, suffer from certain disadvantages (see Winter & Milstein, 1991 Nature 349:293-9, 1991; Babcook et al., Proc Natl Acad Sci 93:7843-8, 1996). One major disadvantage is that cell fusion is very inefficient, and, as such, the production of a hybridoma for a particular monoclonal antibody that is encoded by only a few antibody producing cells of a host mammal is often not possible.

Polyethylene glycol (PEG) was discovered as an effective "fusogen" for hybridoma production in 1975 (Pontecorvo, Somatic Cell Genet. 1:397-400, 1975) and was rapidly adopted by the scientific community as the fusogen of choice. Current methods of cell fusion have not significantly changed in the last 15 years and most, if not all, routine methods use polyethylene glycol as a fusogen (see Harlow et al, *Antibodies: A Laboratory Manual*, First Edition 1988 Cold Spring Harbor, N.Y.). However, even with the use of polyethylene glycol, hybridoma production is extremely inefficient, and in many cases only a few hundred hybridomas can be produced from a whole animal spleen. As such, the spleens of several animals are often used in order to produce a single monoclonal antibody of interest.

Accordingly, there is a great need for improved methods for cell fusion, particularly for monoclonal antibody production. The present invention addresses this, and other, needs.

Literature

References of interest include U.S. Pat. Nos. 6,420,140, 6,451,598, 6,197,578, and 5,675,063 and the following publications: Shirahata et al. (Methods Cell Biol. 57:111-45, 1998), Nagata et al. (Hybridoma 10:369-78, 1991), Garzelli et al. (Eur J Immunol. 16:584-7, 1986), Ahmad et al. (Eur J Biochem. 268:5667-75, 2001), Dzau et al. (Proc Natl Acad Sci USA. 93:11421-5, 1996), Kudo et al. (J Exp Med. 168: 323-7, 1992), Bates et al (Cell 74:1043-1051, 1993) and Gilbert et al. (J. Virol 69:7410-15, 1995).

SUMMARY OF THE INVENTION

Figure 1:
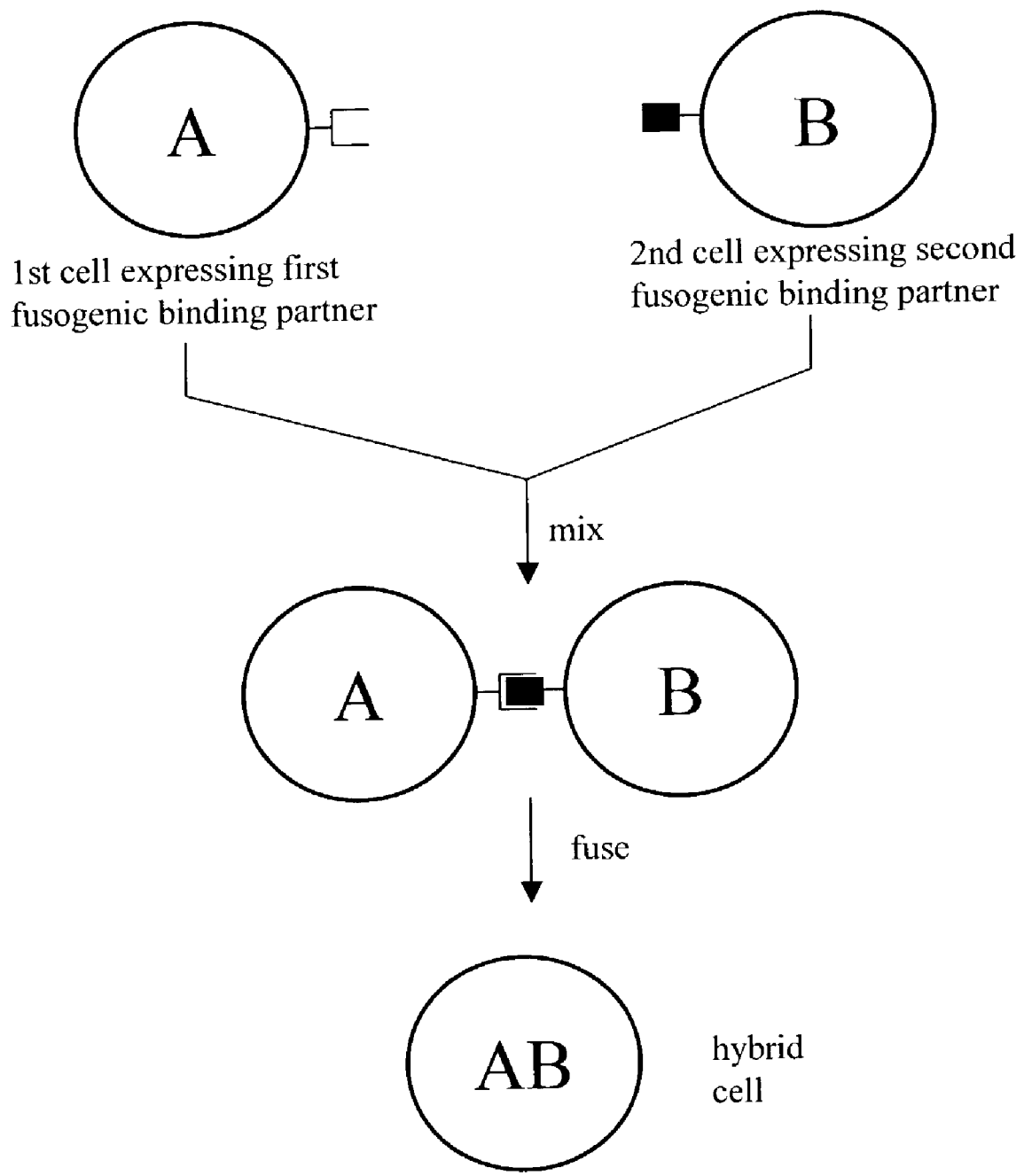
FIG. 1. is a flow chart showing one embodiment of the invention. A first cell expressing a first fusogenic binding partner is fused with a second cell expressing a second fusogenic binding partner to form a hybrid cell.

The invention provides methods for fusing a first cell with a second cell to form a hybrid cell. The methods involve incubating a first parental cell producing a first partner of a fusogenic binding partner pair on its surface with a second parental cell producing a second partner of the fusogenic binding partner pair on its surface. In certain embodiments, the parental cells are incubated with a known fusogen such as polyethylene glycol and the fusogenic binding partner pair increases the rate of cell fusion. In many embodiments, the first cell is an antibody producing cell, the second cell is an immortal cell, and the hybrid cell is a hybridoma cell that produces a monoclonal antibody. Also provided by the invention are methods for producing hybridoma cells, and methods for screening those cells for production of a monoclonal antibody of interest. The invention further provides systems and kits for carrying out the subject methods. The subject methods, systems, and kits find use in a variety of different industrial, medical and research applications.

DEFINITIONS

A "hybrid cell" is cell that is a hybrid of two or more different parental cells. A hybridoma cell that is a hybrid of a spleen cell or other antibody producing cell and an immortal cell (e.g., a myeloma cell) is an example of a hybrid cell. Further examples of hybrid cells and methodologies involved in fusing cells to make hybrid cells may be found in U.S. Pat. No. 6,420,140 and Harlow et al, (*Antibodies: A Laboratory Manual*, First Edition (1988) Cold Spring Harbor, N.Y.).

A "fusogen" is any composition which induces or increases the efficiency of parental cell fusion in the process of making a hybrid cell. Polyethylene glycol is an example of a fusogen known in the art. A fusogen may be described as a "fusogenic" composition.

A "binding partner pair" is any pair of molecules that specifically bind to each other. For example, an antibody and the antigen or epitope to which the antibody binds, or a receptor and the ligand to which the receptor binds are examples of binding partner pairs.

A "polypeptide fusogen" is a proteinaceous composition e.g. an antibody or binding partner pair that is fusogenic. A "fusogenic binding partner pair" is a binding partner pair that is fusogenic. By "fusogenic" is meant facilitating cell fusion. The subject invention involves polypeptide fusogens and fusogenic binding partner pairs.

The terms "antibody" and "immunoglobulin" are used interchangeably herein. These terms refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the terms are Fab', Fv, $F(ab')_2$, and or other antibody fragments that retain specific binding to antigen.

Antibodies may exist in a variety of other forms including, for example, Fv, Fab, and $(Fab')_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988); Bird et al., Science, 242, 423-426 (1988); see Hood et al., "Immunology", Benjamin, N.Y., 2nd ed. (1984), and Hunkapiller and Hood, Nature, 323, 15-16 (1986)).

An immunoglobulin light or heavy chain variable region consists of a "framework" region interrupted by three hypervariable regions, also called "complementarity determining regions" or CDRs. The extent of the framework region and CDRs have been precisely defined (see, "Sequences of Proteins of Immunological Interest," E. Kabat et al., U.S. Department of Health and Human Services, (1983)). The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

Chimeric antibodies are antibodies whose light and heavy chain genes have been constructed, typically by genetic engineering, from antibody variable and constant region genes belonging to different species. For example, the variable segments of the genes from a rabbit monoclonal antibody may be joined to human constant segments, such as gamma 1 and gamma 3. An example of a therapeutic chimeric antibody is a hybrid protein composed of the variable or antigen-binding domain from a rabbit antibody and the constant or effector domain from a human antibody (e.g., the anti-Tac chimeric antibody made by the cells of A.T.C.C. deposit Accession No. CRL 9688), although other mammalian species may be used.

As used herein, unless otherwise indicated or clear from the context, antibody domains, regions and fragments are accorded standard definitions as are well known in the art. See, e.g., Abbas, A. K., et al., (1991) Cellular and Molecular Immunology, W. B. Saunders Company, Philadelphia, Pa.

As used herein, the term "humanized antibody" or "humanized immunoglobulin" refers to an antibody comprising one or more CDRs from an animal antibody, the antibody having being modified in such a way so as to be less immunogenic in a human than the parental animal antibody. An animal antibody can be humanized using a number of methodologies, including chimeric antibody production, CDR grafting (also called reshaping), and antibody resurfacing.

As used herein, the term "murinized antibody" or "murinized immunoglobulin" refers to an antibody comprising one or more CDRs from an animal antibody, the antibody having being modified in such a way so as to be less immunogenic in a mouse than the parental animal antibody. An animal antibody can be murinized using a number of methodologies, including chimeric antibody production, CDR grafting (also called reshaping), and antibody resurfacing.

It is understood that the humanized antibodies designed and produced by the present method may have additional conservative amino acid substitutions which have substantially no effect on antigen binding or other antibody functions. By conservative substitutions is intended combinations such as gly, ala; val, ile, leu; asp, glu; asn, gln; ser, thr; lys, arg; and phe, tyr.

As used herein, the terms "determining," "measuring," and "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

As used herein the term "isolated," when used in the context of an isolated antibody, refers to an antibody of interest that is at least 60% free, at least 75% free, at least 90% free, at least 95% free, at least 98% free, and even at least 99% free from other components with which the antibody is associated with prior to purification.

A "coding sequence" or a sequence that "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences that are immunologically identifiable with a polypeptide encoded by the sequence.

"Operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of a coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes comprising non-native nucleic acid sequences, and the like.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells, which can be accomplished by genomic integration of all or a portion of the vector, or transient or inheritable maintenance of the vector as an extrachromosomal element. Thus, the term includes cloning, and expression vehicles, as well as integrating vectors.

An "expression cassette" comprises any nucleic acid construct capable of directing the expression of a gene/coding sequence of interest, which is operably linked to a promoter of the expression cassette. Such cassettes can be constructed into a "vector," "vector construct," "expression vector," or "gene transfer vector," in order to transfer the expression cassette into target cells. Thus, the term includes cloning and expression vehicles, as well as viral vectors.

Techniques for determining nucleic acid and amino acid "sequence identity" are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

Alternatively, homology can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%-85%, preferably at least about 85%-90%, more preferably at least about 90%-95%, and most preferably at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., infra; *DNA Cloning*, supra; *Nucleic Acid Hybridization*, supra.

Two nucleic acid fragments are considered to "selectively hybridize" as described herein when they detectably pair with each other. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of nonspecific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.). An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5× Denhardt's solution, 10% dextran sulfate, and 20 mg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment of the invention.

A first polynucleotide is "derived from" a second polynucleotide if it has the same or substantially the same nucleotide sequence as a region of the second polynucleotide, its cDNA, complements thereof, or if it displays sequence identity as described above. A first polynucleotide may be derived from a second polynucleotide if the first polynucleotide is used as a template for, e.g. amplification of the second polynucleotide.

A first polypeptide is "derived from" a second polypeptide if it is (i) encoded by a first polynucleotide derived from a second polynucleotide, or (ii) displays sequence identity to the second polypeptides as described above. The term "unit dosage form" as used herein refers to physically discrete units suitable as unitary dosages for subjects (e.g., animals, usually humans), each unit containing a predetermined quantity of an agent, e.g. an antibody in an amount sufficient to produce the desired effect in association with a pharmaceutically acceptable diluent, carrier or vehicle. The specifications for the novel unit dosage forms of the present invention will depend on a variety of factors including, but not necessarily limited to, the particular agent employed and the effect to be achieved, and the pharmacodynamics associated with each compound in the host.

A polynucleotide is "derived from" a particular cell if the polynucleotide was obtained from the cell. A polynucleotide may also be "derived from" a particular cell if the polynucleotide was obtained from the progeny of the cell, as long as the polynucleotide was present in the original cell. As such, a single cell may be isolated and cultured, e.g. in vitro, to form a cell culture. A nucleotide isolated from the cell culture is "derived from" the single cell, as long as the nucleic acid was present in the isolated single cell.

The terms "treatment" "treating" and the like are used herein to refer to any treatment of any disease or condition in a mammal, e.g. particularly a human or a mouse, and includes: a) preventing a disease, condition, or symptom of a disease or condition from occurring in a subject which may be predisposed to the disease but has not yet been diagnosed as having it; b) inhibiting a disease, condition, or symptom of a disease or condition, e.g., arresting its development and/or delaying its onset or manifestation in the patient; and/or c) relieving a disease, condition, or symptom of a disease or condition, e.g., causing regression of the condition or disease and/or its symptoms.

The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

Before the present invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an antibody" includes a plurality of such antibodies and reference to "a variable domain" includes reference to one or more variable domains and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF PREFERRED EMBODIMENTS

The invention provides methods for fusing a first cell with a second cell to form a hybrid cell. The methods involve incubating a first parental cell producing a first partner of a fusogenic binding partner pair on its surface with a second parental cell producing a second partner of the fusogenic binding partner pair on its surface. In certain embodiments, the parental cells are incubated with a known fusogen such as polyethylene glycol and the fusogenic binding partner pair increases the rate of cell fusion. In many embodiments, the first cell is an antibody producing cell, the second cell is an immortal cell, and the hybrid cell is a hybridoma cell that produces a monoclonal antibody. Also provided by the invention are methods for producing hybridoma cells, and methods for screening those cells for production of a monoclonal antibody of interest. The invention further provides systems and kits for carrying out the subject methods. The subject methods, systems, and kits find use in a variety of different industrial, medical and research applications.

In further describing the subject invention, the methods of the invention will be described first, followed by a review of the representative applications in which the subject systems find use as well as a review of the subject systems and kits that may be employed to practice the subject methods.

Methods of Making Hybrid Cells

The invention provides a method of making a hybrid cell by fusion of two parental cells. In general, the method involves fusion of a first parental cell producing the first partner of a binding partner pair on its surface and a second parental cell producing the second partner of a binding partner pair on its surface. The methods usually involve incubating the first and second parental cells and allowing the fusogenic binding partner pair to bind to each other and bring the parental cells into close proximity, thereby stimulating or increasing the rate of cell fusion. FIG. 1 schematic describes this method.

The subject method may be performed in the presence or absence of a known fusogen. In methods performed with a known fusogen, the fusogenic conditions used in the subject fusion methods sometimes involve polyethylene glycol (PEG), however, any suitable fusogenic conditions, e.g., those that are electrofusion (e.g., electroporation), viral (e.g., EBV or Sendai virus), or liposome-mediated may also be used. Suitable fusogenic conditions are known in the art and are described in several publications, such as U.S. Pat. No. 6,420,140, Harlow et al, (*Antibodies: A Laboratory Manual*, First Edition (1988) Cold Spring Harbor, N.Y.), Ramos et al, (Anal. Biochem 302:213-219, 2002), Jantscheff et al (Cancer Immunol. Immunother. 51:367-375, 2002).

When the subject methods involve a known fusogen, the presence of a binding partner pair on the surface of the parental cells increases the efficiency of parental cell fusion. For example, the efficiency of parent cell fusion may include an increase in the rate at which cells fuse, or may include an increase in the number of cells that fuse under a pre-defined or unlimited time. For example, an increase in efficiency of more than about 10%, more than about 20%, more than about 40%, more than 60%, more than about 80%, more than about 100%, more than about 150%, more than about 200%, more than about 300%, more than about 500%, or more than about 10×, more than about 20× or more than about 50×, 100× or 1000× or more may be observed, as compared to the fusion efficiency of cells in the absence of a binding partner pair. For example, parent cell fusion may occur at a rate that is 100 times (100×) faster and/or may happen to 100 times more cells in the presence of a binding partner pair as compared to cells in the absence of a binding partner pair.

In certain embodiments, the subject methods do not involve known fusogens. In these embodiments, the fusogenic binding partner pair induces cell fusion when cell fusion would not have been significant in the absence of the fusogenic binding partner pair. In these embodiments, more than about 0.001% of the cells of a first parental cell populations fuse with cells of the second parental cell population. In many embodiments, however, more than about 0.005%, more than about 0.01%, more than about 0.02%, more than about 0.05%, or more than about 0.1% or more of cells of at least one of the parent cell populations fuse with cells of the other parental cell population. In embodiments of the subject methods that do not involve known fusogens, parent cell fusion may also be measured relative to the rate cell fusion of similar or identical parent cells in the presence of a known fusogen, e.g. PEG. In these embodiments, a fusogenic binding partner pair may result in a rate of cell fusion that is more than about 10%, more than about 20%, more than about 40%, more than 60%, more than about 80%, more than about 100%, more than about 150%, more than about 200%, more than about 300%, more than about 500%, or more than about 10×, more than about 20× or more than about 50×, 100× or 1000× or more greater than the rate of cell fusion of identical parent cells in the presence of the known fusogen.

In certain embodiments, the production of at least one of the fusogenic binding pair partners is transient. These embodiments usually involve producing at least one of the fusogenic binding pair partners on one of the parental cells prior to mixing and incubation with the other parental cell (in the presence or absence of a known fusogen), and at least decreasing the levels of a fusogenic binding pair partner once a hybrid cell has been formed. Such transient expression methods usually involve transiently expressing at least one fusogenic binding pair partner using a vector construct with an inducible promoter, methods for making and using of which are further described below.

Parental Cells

The subject methods involve at least a pair of parental cells, i.e., a first and a second parental cell, that fuse to form a hybrid cell. In many embodiments, the first parental and second parental cells are suitable for fusion to each other and each parental cell usually has one or more desirable characteristics, such as expression of a particular polypeptide, e.g. an antibody, an ability to produce large amounts of polypeptide, an ability to process and/or present antigens, an ability to interact with other cells, immortality, amenity to genetic manipulation, etc. The first parental cell and the second parental cells are usually different (i.e. non-identical) cells, derived from the same species of organism, e.g., bacteria, fungi, animals (including mammals such as humans, mouse, rats, sheep, goats, chickens rabbits, cows and the like) and plants.

In one embodiment the first parental cell is a cell that produces a monoclonal antibody, e.g. a spleen cell, and the second parental cell is an immortalized cell derived from the same species as the first parental cell. Examples of suitable immortal parental cells, e.g., myeloma cells, are known in the art and include the mouse derived P3/X63-Ag8.653, P3/NS1/1-Ag4-1(NS-1), P3/X63Ag8.U1 (P3U1), SP2/O—Ag14 (Sp2/O, Sp2), PAI, F0, and BW5147; rat derived 210RCY3-Ag.2.3; human derived U-266AR1, GM1500-6TG-A1-2, UC729, CEM-AGR, DIR11, and CEM-T15; chicken derived DT-40; and rabbit derived 240E cells.

An antibody-producing cell is a cell that produces antibodies. Such cells are typically cells involved in a mammalian immune response, such as a B-lymphocyte or its progeny including the plasma cell, and usually produce immunoglobulin heavy and light chains that have been "naturally paired" by the immune system of the host. These cells are usually antibody-secreting cells. In most embodiments, the cell is an antibody producing cell that produces a monoclonal antibody, the binding specificity for which is usually unknown until the hybrid cells are screened.

An antibody-producing cell may be obtained from an animal which has not been immunized with a selected antigen, which has been immunized with a selected antigen, or which has developed an immune response to an antigen as a result of disease or condition. Animals may be immunized with a selected antigen using any of the techniques well known in the art suitable for generating an immune response (see Handbook of Experimental Immunology D. M. Weir (ed.), Vol 4, Blackwell Scientific Publishers, Oxford, England, 1986). Within the context of the present invention, the phrase "selected antigen" includes any substance to which an antibody may be made, including, among others, proteins, carbohydrates, inorganic or organic molecules, transition state analogs that resemble intermediates in an enzymatic process, nucleic acids, cells, including cancer cells, cell extracts, pathogens, including living or attenuated viruses, bacteria and the like. As will be appreciated by one of ordinary skill in the art, antigens which are of low immunogenicity may be accompanied with an adjuvant or hapten in order to increase the immune response (for example, complete or incomplete Freund's adjuvant) or with a carrier such as keyhole limpet hemocyanin (KLH).

Many warm-blooded animals, in particular mammals such as humans, rabbits, mice, rats, sheep, cows or pigs and aves such as chickens and turkeys, may be used in order to obtain antibody-forming cells. However, rabbits and mice are generally preferred because of their ease in handling, well-defined genetic traits, and the fact that they may be readily sacrificed. Procedures for immunizing animals are well known in the art, and are described in Harlow et al, (*Antibodies. A Laboratory Manual*, First Edition (1988) Cold Spring Harbor, N.Y.). Antibody-producing cells may also be obtained from a subject which has generated the cells during the course of a selected disease or condition. For instance, antibody-producing cells from a human with a disease of unknown cause, such as rheumatoid arthritis, may be obtained and used in an effort to identify antibodies which have an effect on the disease process or which may lead to identification of an etiological agent or body component that is involved in the cause of the disease. Similarly, antibody-producing cells may be obtained from subjects with disease due to known etiological agents such as malaria or AIDS. These antibody-producing cells may be derived from the blood, lymph nodes or bone marrow, as well as from other diseased or normal tissues. Antibody-producing cells may also be prepared from blood collected with an anticoagulant such as heparin or EDTA. The antibody-producing cells may be further separated from erythrocytes and polymorphs using standard procedures such as centrifugation with Ficoll-Hypaque (Pharmacia, Uppsula, Sweden). Antibody-producing cells may also be prepared from solid tissues such as lymph nodes or tumors by dissociation with enzymes such as collagenase and trypsin in the presence of EDTA.

Antibody-producing cells may also be obtained by culture techniques such as in vitro immunization. Examples of such methods are described Reading in Methods in Enzymology (21:18-33 J. J. Langone, H. H. van Vunakis (eds.), Academic Press Inc., N.Y.; 1986). Briefly, a source of antibody-producing cells, such as a suspension of spleen or lymph node cells, or peripheral blood mononuclear cells are cultured in medium such as RPMI 1640 with 10% fetal bovine serum and a source of the substance against which it is desired to develop antibodies. This medium may be additionally supplemented with amounts of substances known to enhance antibody-forming cell activation and proliferation such as lipopolysaccharide or its derivatives or other bacterial adjuvants or cytokines such as IL-1, IL-2, IL-4, IL-5, IL-6, GM-CSF, and IFN-gamma. To enhance immunogenicity, the selected antigen may be coupled to the surface of cells, for example, spleen cells, by conventional techniques such as the use of biotin/avidin.

Once a suitable animal containing an antibody-producing cell has been identified or produced, spleen, lymph node or bone marrow tissue is typically removed, and a cell suspension of antibody-producing cells is prepared using techniques well known in the art. In most embodiments, this suspension is a single cell suspension, techniques for the preparation of which are well known in the art, e.g., Harlow et al, (*Antibodies: A Laboratory Manual*, First Edition (1988) Cold Spring Harbor, N.Y.).

Antibody-producing cells may be enriched from the single cell suspension by methods based upon the size or density of the antibody-forming cells relative to other cells. An example of the use of Percoll to separate cells according to density is described by van Mourik and W. P. Zeizlmaker in Methods in Enzymology 121:174-182 (J. J. Langone, H. H. van Vunakis (eds.), Academic Press Inc., N.Y.). Gradients of varying density of solutions of bovine serum albumin can also be used to separate cells according to density. (See N. Moav and T. N. Harris, J. Immunol 105:1512, 1970; see also Raid, D. J. in SELECTED METHODS IN CELLULAR IMMUNOLOGY, B. Mishell and S. Shiigi (eds.), W. H. Freeman and Co., San Francisco, 1987). Antibody-producing cells may also be enriched and plated using other methods. Exemplary antibody-producing cell enrichment methods include performing flow cytometry (FACS) of cell populations obtained from rabbit spleen, bone marrow, lymph node or other lymph organs, e.g., through incubating the cells with labeled anti-rabbit IgG and sorting the labeled cells using a FACSVantage SE cell sorter (Becton-Dickinson, San Jose, Calif.).

In certain embodiments, the antibody-producing cells are not further selected based on the specificity of the antibodies that are expressed by the antibody-producing cells. As such, typically, antibody producing cells are used directly after enrichment, and are not subject to any further purification or selection based on the reactivity or specificity of the antibodies being expressed by the antibody producing cell. In these embodiments, the antibody-producing cells are of "unknown" specificity because the antigen (i.e. the protein, pathogen, peptide, cell, cell extract, nucleic acid, carbohydrate etc.) to which the antibodies of the antibody producing cells bind is not determined. In certain other embodiments, antibody-producing cells are further selected based on the specificity of the antibodies that are expressed.

Fusogenic Binding Partners

The subject methods involve a fusogenic binding partner pair. A fusogenic binding partner pair is any two binding partners that may each be individually expressed on the surface of parental cells such that a first partner of a fusogenic binding pair is present on the surface of a first parental cell and a second partner of the fusogenic binding pair is present on the surface of a second parental cell. Such fusogenic binding partner pairs increase the rate of parental cell fusion, or stimulates the parental cells to fuse, depending on how cell fusion is measured. In other words, a fusogenic binding partner pair is any pair of molecules that specifically bind to each other that can stimulate cell fusogen.

Fusogenic binding partners are usually peptides or proteins that bind to each other with high avidity and/or specificity. In general, fusogenic binding partners bind each other with a binding affinity of about $10^{-6}$ M or more, about $5 \times 10^{-7}$ M or more, about $10^{-7}$ M or more, about $5 \times 10^{-8}$ M or more, about $10^{-8}$ M or more, about $5 \times 10^{-9}$ M or more, about $10^{-9}$ M or more, about $5 \times 10^{-8}$ M or more, about $10^{-10}$ M or more, about $5 \times 10^{-11}$ M or more, about $10^{-11}$ M or more, about $5 \times 10^{-12}$ M or more, about $10^{-12}$ M or more, about $5 \times 10^{-13}$ M or more. Fusogenic binding partners are usually present on the surface of the parental cells such that they may interact and bind to each other. For example, a binding partner may be tethered or anchored to the plasma membrane of a parental cell using a hydrophobic transmembrane domain, or may itself specifically bind a molecule anchored to the surface of the cell.

In some embodiments, a binding partner e.g., an antibody, may be present on the surface via a non-covalent specificic interaction between a portion of the binding partner (e.g. an antigen binding portion of an antibody) and a cell surface molecule (e.g. an antigen). For example, a divalent antibody may be a binding partner that is bound to the surface of a parent cell by one of its Fab regions binding a molecule on the surface of the second parental cell. The other Fab region of the divalent antibody may bind a second binding partner on the surface of the other parent cell. Another example is an antibody that is modified, e.g., with biotin, such that it specifically binds a parental cell, e.g., one that expresses streptavidin. In this example, the antigen binding portion of the modified antibody bind a second binding partner on the surface of the second parental cell. As such, a bivalent antibody that binds both parental cells, or an antibody that binds both parental cells, or any other molecular fusogen that binds two parental cells, may be considered one partner of a binding partner pair, even if is not covalently bonded to the surface of one of the parental cell.

Each partner of the partner pair usually contains at least one polypeptide chain. In some embodiments, a partner consists of a single polypeptide chain. In other embodiments, a partner consists of multiple polypeptide chains, which may exist as a multi-subunit entity (e.g. an antibody, receptor, or other complex of polypeptides). A partner may be endogenous to a parental cell if it is usually found at the surface of an unmodified parental cell at levels sufficient to bind its binding partner and facilitate cell fusion. A partner may be exogenous to a parental cell if it is not usually found at the surface of an unmodified parental cell at levels sufficient to bind its binding partner and facilitate cell fusion. An exogenous partner may be supplied to the cell using recombinant means. In performing the subject methods, at least one partner (i.e. one or both partners) of a fusogenic binding partner pair is usually produced using recombinant means in the parental cells.

One example of a suitable fusogenic binding partner pair is a viral fusion protein complex and its cellular receptor. Such viruses are usually enveloped viruses that directly fuse with the plasma membrane at neutral pH. Table 1 indicates a number of viral families, examples of viruses and fusion protein that may be used in the subject methods.

TABLE 1

| | viral fusogens | |
|---|---|---|
| Family | Example | Fusion protein |
| Retrovirus | HIV | SU/TM |
| Paramyxovirus | Sendai | F1/F2 |
| Herpesvirus | HSV-1 | gB/D/H/L |
| Coronavirus | MHV | S1/S2 |
| Hepadnavirus | Hepatitis B | S |
| Poxvirus | Vaccinia | 14kDa, 56dDa |

The virus families listed in Table 1 fuse directly with host cells using a fusion protein that may contain multiple polypeptides. Such viral fusion proteins act as fusogens when expressed in a parent cells. In many embodiments, all subunits of a viral fusion protein (e.g. SU and TM), should be expressed in the parental cell in order to facilitate cell fusion, however, in certain embodiments, only one subunit (e.g. SU) may suffice. In certain embodiments, the viral fusion protein expression is sufficient for cell fusion.

For retroviruses, fusion protein is synthesized as a single envelope glycoprotein (Env) that is proteolytically processed into SU and transmembrane TM subunits to facilitate fusion. Within the retroviruses, the avian leucosis and sarcoma virus Env glycoprotein is processed into the SU and TM subunits. The host cell receptor for this virus is TVA, a small transmembrane protein whose extracellular domain consists of a single low-density lipoprotein receptor repeat motif followed by a short linker region (Bates et al Cell 74:1043-1051, 1993 and Gilbert et al 69: J. Virol 69:7410-15, 1995). As such, one fusogenic binding pair is represented by the avian leucosis and sarcoma virus Env glycoprotein SU and TM subunits, and TVA.

For human immunodeficiency virus (HIV), another retrovirus, the envelope glycoprotein is thought to be a trimer or tetramer of SU (gp120) and TM (gp41). Gp120 is responsible for binding to CD4, the primary HIV receptor, and gp41 is responsible for fusion activity. CD4 is a single membrane-spanning T-cell surface glycoprotein that normally functions in initiating T-cell activation. For HIV, the virion attachment protein, gp120, attaches initially to the CD4 protein on a helper T-cell. The gp120 undergoes conformational change due to binding, and binds the accessory receptor, CCR-5, a chemokine receptor. This binding induces gp41 to bind the cell membrane, and facilitate membrane fusion. As such, a further fusogenic binding pair is represented by the HIV gp120/gp41 subunits, and the cellular CD4/CCR-5 proteins.

For murine leukemia virus, another retrovirus, the ecotropic fusion peptide receptor protein, MCAT-1, is a multi-membrane spanning cationic amino acid transporter, and the amphotropic receptor is a phosphate transporter protein related to the gibbon ape leukemia virus receptor (Kavanaugh PNAS 91: 7071-7075, 1994). Since MCAT-1 expression alone is sufficient for MLV infection, further factors are not required for cell fusion. As such, MCAT-1 alone may act as a fusogen, with its cellular receptor.

Paramyxoviruses contain at least two envelope glycoproteins, an attachment protein (HN, H or G), and a fusion protein (F). The F protein is proteolytically processed into F1 and F2 subunits which have structural similarities to the retrovirus Env and orthomyxovirus fusion proteins. In certain paramyxoviruses, e.g., SV5, expression of F alone is sufficient for membrane fusion, and for others, coexpression of HN is necessary for fusion. As such, F may act as a fusogen.

Further suitable viral-related fusogenic binding pairs are discussed in the following references: Hernandez et al (Annu. Rev. Cell Dev. Biol. 12:627-661, 1996) and Eckert et al (Annu. Rev. Biochem. 70:777-810, 2001).

A further example of a suitable fusogenic binding partner pair is a cellular receptor and peptide ligand. Receptor ligand pairs are well known in the art and are described in several textbooks such as Alberts et al, (Molecular Biology of the Cell, Fourth Edition Garland Science, 2002). Exemplary suitable receptor ligand pairs are: interleukins and their receptors (e.g. IL-1, IL-2, IL-3, IL-4, IL-5, IL-6, IL-7, IL-8, IL-9, IL-10, IL-11, IL-12, IL-13, IL-14, and IL-15 and their receptors), chemochines and their receptors (e.g. PF4, RANTES, MIP1a, MCP1, IP-10, ENA-78, NAP-2, Groα, Groβ, and IL-8 and their receptors), growth factors and their receptors (e.g., TNFα, TGFβ, TSH, VEGF/VPF, PTHrP, EGF family, FGF, PDGF family, endothelin, fibrosin, laminin, and gastrin releasing peptide, GRP and their receptors), hematopoietins e.g., M-CSF, G-CSF, GM-CSF, and EPO and their receptors.

A further example of a suitable fusogenic binding partner pair is a monoclonal antibody and a peptide antigen to which the antibody specifically binds. When used as a molecular fusogen, the antibody is expressed on the surface of one parental cell (for example, in a similar way to IgM or IgG is expressed on the surface of a B lymphocyte) and the antigen to which the antibody specifically binds is present or produced on the surface of the other parental cell. In this example, if the parental cell is an antibody producing cell, than the monoclonal antibody that is produced on the surface of the of the parental cell to facilitate cell fusion is different to the monoclonal antibody that is endogenously produced by the antibody-producing cell. In other words, if a fusogenic binding partner pair involves an antibody-producing cell and a monoclonal antibody and a peptide antigen fusogenic binding partner pair, then the antibody-producing cell may produce two monoclonal antibodies, one secreted and the other on cell surface.

One of skill in the art would recognize that there are several molecular fusogens other than those described above. For example, it would be recognized that two different subunits of a multi-subunit protein that bind to each other could act as a fusogen. It would further be recognized that fusogenic binding partner pairs could be identified by several different methods which detect protein-protein interactions. These methods include the yeast two hybrid method (Ausubel, et al, Short Protocols in Molecular Biology, 3rd ed., Wiley & Sons, 1995 and Sambrook, et al, Molecular Cloning: A Laboratory Manual, Third Edition, 2001 Cold Spring Harbor, N.Y.). In many embodiments, however, molecular fusogens that involve antibodies, receptor-ligand pairs and viral fusion proteins are used.

Figure 2:
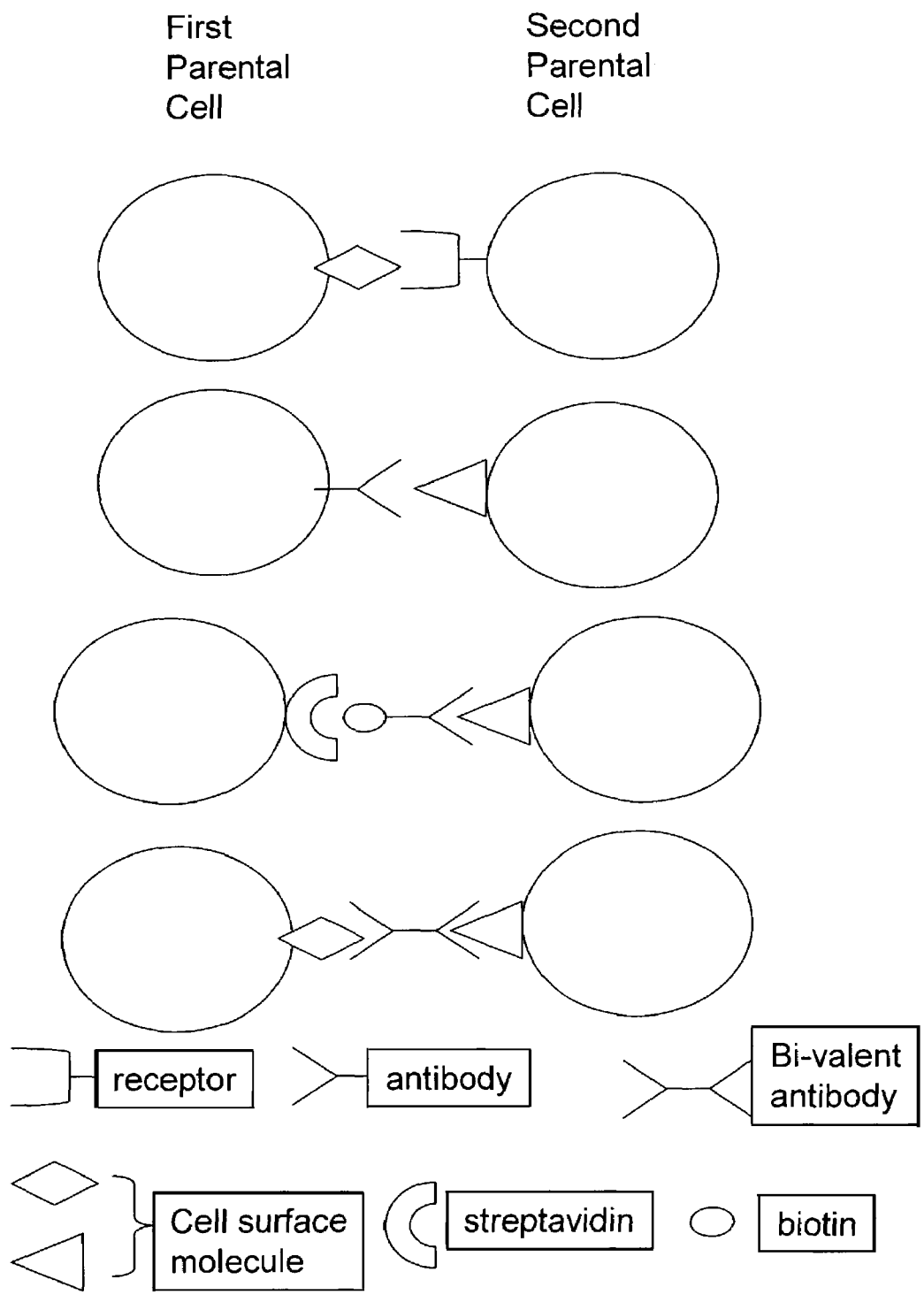
FIG. 2. is a schematic figure showing various embodiments of the invention.

In an alternative embodiment, an "adaptor" fusogen many be used to bring two parental cells together to facilitate fusion of the two parental cells. An example of such an "adaptor" fusogen is a bi-specific antibody or "diabody" (Kipriyanov, Methods Mol Biol. 178:317-31 (2002); Kriangkum et al, Biomol Eng. 18:31-40 (2001); Weiner, Cancer J. May; 6 Suppl 3:S265-71 (2000)). Bi-specific antibodies recognize and bind two different antigens. When used as a fusogen, a single bi-specific antibody binds two parental cells via epitopes present on the surface of the parental cells and cause the cells to be in close proximity. For example, one Fab fragment (i.e. one of the two different antigen binding fragments) of a bi-specific antibody binds to an antigen (e.g., a marker) on the surface of one parental cell and the other Fab fragment binds to a different antigen on the surface of the other parental cell. The antigens on the surface of the parental cells may be endogenous antigens, or antigens produced by recombinant means. In certain embodiments, the antibody recognizes the same antigen on both of the parental cells. Antibodies have certain advantages as a fusogen because they can be added to a mixture of cells, and later removed from solution by washing after cell fusion has taken place. Various embodiments of the invention are shown in FIG. 2.

In certain embodiments when an adaptor fusogen is used, streptavidin may be produced on the cell surface of one parental cell. In these embodiments, an adaptor fusogen conjugated to biotin will bind the streptavidin on the surface of that cell, and also bind a suitable binding partner on the surface of a second parental cell and binds both parental cells together.

If a parent cell lacks or contains an insufficient amount of a fusogenic binding partner (or antigen) on its surface, the binding partner may be produced using a recombinant expression cassette containing binding partner-encoding sequences introduced into the cell. The expression cassette, including a suitable promoter (e.g., inducible promoters) terminators, enhancers, translation initiation signals, translational enhancers, are well known in the art, and are discussed in Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.). Suitable promoters include SV40 elements, as described in Dijkema et al., EMBO J. (1985) 4:761; transcription regulatory elements derived from the LTR of the Rous sarcoma virus, as described in Gorman et al., Proc. Nat'l Acad. Sci USA (1982) 79:6777; transcription regulatory elements derived from the LTR of human cytomegalovirus (CMV), as described in Boshart et al., Cell (1985) 41:521; hsp70 promoters, (Levy-Holtzman, R. and I. Schechter (Biochim. Biophys. Acta (1995) 1263: 96-98) Presnail, J. K. and M. A. Hoy, (Exp. Appl. Acarol. (1994) 18: 301-308)) and the like. Suitable inducible promoters include the tetracycline inducible promoters (e.g., Reeves et al, Proc Natl Acad Sci USA. 99:13413-8, 2002), steroid inducible promoters such as the glucocorticoid promoter (e.g., Mader et al, Proc Natl Acad Sci USA. 90:5603-7, 1993; Israel et al, Nucleic Acids Res. 17:4589-604, 1989) and heat and stress inducible promoters (e.g., Walther et al, Int J Cancer. 98:291-6, 2002). The expression cassette provides for expression of a binding partner in a host cell. In most embodiments, each expression cassette is more than about 0.5 kb in length, more than about 1.0 kb in length, more than about 1.5 kb in length, more than about 2 kb in length, more than about 4 kb in length, more than about 5 kb in length, and is usually less than 10 kb in length. In most embodiments, a fusion partner is expressed without the compositions (e.g. polypeptides and polynucleotides) with which it is usually associated. For example, a fusion partner that is virally derived is expressed in the absence of other viral proteins such as a polymerase, protease or coat protein.

The expression cassette may be linear, or encompassed in a circular vector, which may further comprise a selectable marker. Suitable vectors, e.g., viral and plasmid vectors, and selectable markers are well known in the art and discussed in Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.). A variety of different genes have been employed as selectable markers, and the particular gene employed in the subject vectors as a selectable marker is chosen primarily as a matter of convenience. Known selectable marker genes include: the thimydine kinase gene, the dihydrofolate reductase gene, the xanthineguanine phosporibosyl transferase gene, CAD, the adenosine deaminase gene, the asparagine synthetase gene, the antibiotic resistance genes, e.g., tetr, ampr, Cmr or cat, kanr or neor (aminoglycoside phosphotransferase genes), the hygromycin B phosphotransferase gene, and the like. Vectors may provide for integration into the host cell genome, or may be autonomous from the host cell genome.

In certain embodiments, an expression cassette further provides for targeting of the antigen to the surface of the host cell by producing an antigen operably linked to a cell surface targeting polypeptide. In such embodiments, the antigen encoding nucleic acid may be operably linked to a cell surface targeting polypeptide-encoding nucleic acid in the expression cassette, and transcription and subsequent translation of the nucleic acids provides for production of a fusion protein containing the antigen and the cell surface targeting polypeptide. As such, the expression cassette can provide for targeting of an antigen to the surface of a host cell, which antigen is not usually presented on the surface of the host cell. Suitable cell surface targeting polypeptides and their encoding nucleic acid sequences may be those of, for example, transmembrane serine threonine or tyrosine kinase receptors. Suitable cell surface targeting signals and their encoding nucleic acid sequences include receptor transmembrane domains, such as the epidermal growth factor receptor (EGFR) transmembrane domain (Ullrich, A. et al. Nature 309: 418-425 (1984)). In many embodiments involving a partner that is usually surface bound (e.g. a transmembrane receptor or membrane bound antibody), no cell surface targeting signal is required to target the molecule to the surface of a cell. Further examples of strategies for targeting of polypeptides in a cell or protein secretion may be found in U.S. Pat. No. 6,455,247.

In many embodiments the expression cassette is present in a vector containing a vector backbone that is bacterial in origin and does not contain a significant of viral derived sequences. In these embodiment, the vector does not encode an infectious agent (e.g. a virus). In many embodiments, the expression products of the vector are not toxic to the cell, and do not significantly inhibit cell division, cell metabolism and the like.

Expression cassettes may be introduced into a host cell using a variety of methods, including viral infection, transfection, conjugation, protoplast fusion, electroporation, particle gun technology, calcium phosphate precipitation, direct microinjection, viral vector delivery, and the like. The choice of method is generally dependent on the type of cell being transformed and the circumstances under which the transformation is taking place (i.e., in vitro). A general discussion of these methods can be found in Ausubel, et al, Short Protocols in Molecular Biology, 3rd ed., Wiley & Sons, 1995.

In certain embodiments, a transgenic animal that produces one of the binding partners on the surface of suitable cells, e.g., spleen cells, may be used as a host animal for immunizations. This reduces the need to introduce a binding partner into an isolated spleen cell by recombinant means.

In most embodiments, a binding partner is a polypeptide, and the polypeptide is from about 9 to about 15 amino acids in length, about 16 to about 40 amino acids in length, about 41 to about 60 amino acids in length, about 61 to about 100 amino acids in length, about 101 to about 200 amino acids in length, about 201 to about 300 amino acids in length, about 301 to about 400 amino acids in length, about 401 to about 500 amino acids in length, usually less than about 1000 amino acids in length.

Hybrid Cells

The subject methods involve the fusion of parental cells each expressing a partner of a fusogenic pair of binding partners to form a hybrid cell. In most embodiments, the hybrid cell possesses the desirable characteristics of both of the parental cells. For example, if the first parental cell is an antibody-producing rabbit spleen cell and the second parental cell is an immortal rabbit 240E cell, the hybrid cell is immortal and secretes a monoclonal antibody. Such immortal, antibody-producing cells are termed "hybridoma" cells. Antibodies produced by such cells are termed "monoclonal" antibodies.

In embodiments where a hybridoma cell is produced, the antigen binding characteristics (e.g. specificity, avidity, etc) of the monoclonal antibody produced is normally unknown at the point of making the hybridoma. At the time of parental cell fusion, a fusogenic pair of binding partners is usually present on the surface of the subject hybrid cells.

Methods for selection of hybrid cells from a composition containing at least two parental cells are well known in the art (e.g. Harlow et al, *Antibodies: A Laboratory Manual*, First Edition (1988) Cold Spring Harbor, N.Y.). In some embodiments, selection of fused or hybrid cells can be initially determined through the utilization of distinct marker genes in each of the parental cells. Hybrid cells can be further selected based upon expression levels of immunoglobulin molecules, as will be further discussed below.

Screening Methods

The invention provides a method of screening a plurality of monoclonal antibodies produced by hybrid cells. In general, this method involves producing a plurality of hybrid cells producing monoclonal antibodies using the method described above, and screening the plurality of monoclonal antibodies using one or a combination of a variety of assays. In general, these assays are functional assays, and may be grouped as follows: assays that detect an antibody's binding affinity or specificity, and assays that detect the ability of an antibody to inhibit a process.

A monoclonal antibody identified as having a specific binding activity with an antigen, or an inhibitory activity is termed a monoclonal antibody of interest.

Binding Assays

In these assays, antibodies are tested for their ability to bind specifically to a substrate. The term "specifically" in the context of antibody binding, refers to high avidity and/or high affinity binding of an antibody to a specific antigen i.e., a polypeptide, or epitope. In many embodiments, the specific antigen is an antigen (or a fragment or subfraction of an antigen) used to immunize the animal host from which the antibody-producing cells were isolated. Antibody specifically binding an antigen or fragment thereof is stronger than binding of the same antibody to other antigens. Antibodies which bind specifically to a polypeptide may be capable of binding other polypeptides at a weak, yet detectable, level (e.g., 10% or less of the binding shown to the polypeptide of interest). Such weak binding, or background binding, is readily discernible from the specific antibody binding to a subject polypeptide, e.g. by use of appropriate controls. In general, specific antibodies bind to an antigen with a binding affinity of $10^{-7}$ M or more, e.g., $10^{-8}$ M or more (e.g., $10^{-9}$ M, $10^{-10}$, $10^{-11}$, etc.). In general, an antibody with a binding affinity of $10^{-6}$ M or less is not useful in that it will not bind an antigen at a detectable level using conventional methodology currently used.

Typically, in performing a screening assay, antibody samples produced by a library of antibody producing host cells are deposited onto a solid support in a way that each antibody can be identified, e.g. with a plate number and position on the plate, or another identifier that will allow the identification of the host cell culture that produced the antibody.

The antibodies of the invention may be screened for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally involve lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4.degree. C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads).

Western blot analysis generally involves preparation of protein samples followed by electrophoresis of the protein samples in a polyacrylamide gel (e.g., 8%-20% SDS-PAGE depending on the molecular weight of the antigen), and transfer of the separated protein samples from the polyacrylamide gel to a membrane such as nitrocellulose, PVDF or nylon. Following transfer, the membrane is blocked in blocking solution (e.g., PBS with 3% BSA or non-fat milk), washed in washing buffer (e.g., PBS-Tween 20), and incubated with primary antibody (the antibody of interest) diluted in blocking buffer. After this incubation, the membrane is washed in washing buffer, incubated with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I), and after a further wash, the presence of the antigen may be detected. One of skill in the art would be knowledgeable as to the parameters that can be modified to increase the signal detected and to reduce the background noise.

ELISAs involve preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Antibodies of the invention may be screened using immunocytochemisty methods on cells (e.g., mammalian cells, such as CHO cells) transfected with a vector enabling the expression of an antigen or with vector alone using techniques commonly known in the art. Antibodies that bind antigen transfected cells, but not vector-only transfected cells, are antigen specific.

In certain embodiments, however, the assay is an antigen capture assay, and an array or microarray of antibodies may be employed for this purpose. Methods for making and using microarrays of polypeptides are known in the art (see e.g. U.S. Pat. Nos. 6,372,483, 6,352,842, 6,346,416 and 6,242,266).

Inhibitor Assays

In certain embodiments, the assay measures the specific inhibition of an antibody to an interaction between a first compound and a second compound (e.g. two biopolymeric compounds) or specifically inhibits a reaction (e.g. an enzymatic reaction). In the interaction inhibition assay, one interaction substrate, usually a biopolymeric compound such as a protein e.g. a receptor, may be bound to a solid support in a reaction vessel. Antibody is added to the reaction vessel followed by a detectable binding partner for the substrate, usually a biopolymeric compound such as a protein e.g. a radiolabeled ligand for the receptor. After washing the vessel, interaction inhibition may be measured by determining the amount of detectable binding partner present in the vessel. Interaction inhibition occurs when binding of the binding partner is reduced greater than about 20%, greater than about 50%, greater than about 70%, greater than about 80%, or greater than about 90% or 95% or more, as compared to a control assay that does not contain antibody.

In the reaction inhibition assay, an enzyme may be bound to a solid support in a reaction vessel. Antibody is usually added to the reaction vessel followed by a substrate for the enzyme. In many embodiments, the products of the reaction between the enzyme and the substrate are detectable, and, after a certain time, the reaction is usually stopped. After the reaction has been stopped, reaction inhibition may be measured by determining the level of detectable reaction product present in the vessel. Reaction inhibition occurs when the rate of the reaction is reduced greater than about 20%, greater than about 50%, greater than about 70%, greater than about 80%, or greater than about 90% or 95% or more, as compared to a control assay that does not contain antibody.

In Vivo Assays

In certain embodiments the monoclonal antibodies are tested in vivo. In general, the method involves administering a subject monoclonal antibody to an animal model for a disease or condition and determining the effect of the monoclonal antibody on the disease or condition of the model animal. In vivo assays of the invention include controls, where suitable controls include a sample in the absence of the monoclonal antibody. Generally a plurality of assay mixtures is run in parallel with different antibody concentrations to obtain a differential response to the various concentrations. Typically, one of these concentrations serves as a negative control, i.e. at zero concentration or below the level of detection.

A monoclonal antibody of interest is one that modulates, i.e., reduces or increases a symptom of the animal model disease or condition by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the antibody. In general, a monoclonal antibody of interest will cause a subject animal to be more similar to an equivalent animal that is not suffering from the disease or condition. Monoclonal antibodies that have therapeutic value that have been identified using the methods and compositions of the invention are termed "therapeutic" antibodies.

Since a hybrid cell expressing an antibody of interest contains immunoglobulin heavy and light chain-encoding nucleic acids, the nucleic acids encoding the monoclonal antibody of interest may be identified if the host cell expressing the monoclonal antibody of interest is identified. As such, the subject nucleic acids may be identified by a variety of methods known to one of skill in the art. Similar methods are used to identify host cell cultures in monoclonal antibody production using hybridoma technology (Harlow et al., *Antibodies: A Laboratory Manual*, First Edition (1988) Cold spring Harbor, N.Y.).

For example, upon identifying a monoclonal antibody of interest, the host cell expressing the antibody of interest may be identified using a "look-up" table which lists, for every antibody sample, the corresponding host cell culture. In certain other embodiments, a look-up table containing antibody library sample identifiers, corresponding expression cassette library sample identifiers and/or host cell identifiers may be used to identify the subject nucleic acids.

Once identified, the nucleic acids encoding a monoclonal antibody of interest may be recovered, characterized and manipulated using techniques familiar to one of skill in the art (Ausubel, et al, Short Protocols in Molecular Biology, 3rd ed., Wiley & Sons, (1995) and Sambrook, et al, Molecular Cloning: A Laboratory Manual, Third Edition, (2001) Cold Spring Harbor, N.Y.).

Methods of Producing a Monoclonal Antibody of Interest

The invention provides several methods of producing a monoclonal antibody of interest. In general these methods involve incubating a host cell containing a nucleic acid encoding a monoclonal antibody of interest under conditions sufficient for production of the antibody. In many embodiments, the methods of producing a monoclonal antibody of interest involve transferring identified expression cassettes for an monoclonal antibody of interest into a suitable vector, and transferring the recombinant vector into a host cell to provide for expression of the monoclonal antibody. In some embodiments, the subject methods involve transferring at least the variable domain-encoding sequences from the identified heavy and light chains into vectors suitable for their expression in immunoglobulin heavy and light chains. Suitable constant domain-encoding sequences and/or other antibody domain-encoding sequences may be added to the variable domain-encoding sequences at this point. These nucleic acid modifications may also allow for humanization of the subject antibody.

The subject monoclonal antibodies can be produced by any method known in the art for the synthesis of antibodies, in particular, by recombinant expression techniques.

Recombinant expression of a subject monoclonal antibody, or fragment, derivative or analog thereof, usually requires construction of an expression vector containing a polynucleotide that encodes the antibody. Methods which are well known to those skilled in the art can be used to construct expression vectors containing antibody coding sequences and appropriate transcriptional and translational control signals. These methods include, for example, in vitro recombinant DNA techniques and synthetic techniques. As such, the invention provides vectors comprising a nucleotide sequence encoding an antibody molecule of the invention.

The expression vector is transferred to a host cell by conventional techniques and the transfected cells are then cultured to produce a subject antibody. In most embodiments, vectors encoding both the heavy and light chains are co-expressed in the host cell to provide for expression of the entire immunoglobulin molecule.

A variety of host-expression vector systems may be utilized to express a subject monoclonal antibody. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells etc.) harboring recombinant expression constructs containing promoters derived from the genome of mammalian cells (e.g., metallothionein promoter) or from mammalian viruses (e.g., the adenovirus late promoter; the vaccinia virus 7.5K promoter). In many embodiments, bacterial cells such as *Escherichia coli*, and eukaryotic cells are used for the expression of entire recombinant antibody molecules. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express antibodies. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized to express a subject antibody. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). The efficiency of expression may be enhanced by the inclusion of appropriate transcription enhancer elements, transcription terminators, etc. (see Bittner et al., Methods in Enzymol. 153:51-544 (1987)).

For long-term, high-yield production of recombinant antibodies, stable expression may be used. For example, cell lines, which stably express the antibody molecule may be engineered. Rather than using expression vectors which contain viral origins of replication, host cells can be transformed with immunoglobulin expression cassettes and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); TIB TECH 11(5):155-215 (1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981).

The host cell may be co-transfected with two expression vectors of the invention, the first vector encoding a heavy chain derived polypeptide and the second vector encoding a light chain derived polypeptide. The two vectors may contain different selectable markers and origins of replication, which enable equal expression of heavy and light chain polypeptides. Alternatively, a single vector may be used which encodes, and is capable of expressing, both heavy and light chain polypeptides.

Once an antibody molecule of the invention has been produced, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

Utility

The invention provides, inter alia, methods for fusing cells using fusogenic binding partners, compositions containing fused cells with binding partners on their surface, screening methods, methods of identifying a monoclonal antibody of interest and its encoding nucleic acid, and methods for expressing a monoclonal antibody of interest. These methods and compositions have several uses, many of which will be described below.

In one embodiment, the invention provides methods for fusing a cell with a first desirable characteristic (e.g. polypeptide expression, antigen processing, ability to interact with other cells, immortality, etc.) with a cell type with a second desirable characteristic (e.g. polypeptide expression, antigen processing, ability to interact with other cells, immortaility, etc.). In general the resultant hybrid cell displays desirable characteristics of both the parent cells. For example, these methods may be used to fuse a cell expressing a polypeptide of interest with a cell having a desirable characteristic (e.g. immortality) to produce a hybrid cell that both expresses the polypeptide of interest and has the desirable characteristic.

Hybrid cells may be used in protein production (Cho et al, J. Biomed. Sci. 9:631-8, 2002), dendrite cell-based cancer vaccines (Bubenik Int. J. Oncol 18:475-8, 2001), basic research (Dickson et al, EMBO J 2:283-288, 1983) and in the producing of antigen producing cells (Jantscheffet al, Cancer Immunol Immunother 51, 367-75, 2002). Hybrid cells find particular use in monoclonal antibody production for the diagnosis and treatment of diseases.

By treatment is meant at least an amelioration of a symptom associated with the pathological condition afflicting the host, where amelioration is used in a broad sense to refer to at least a reduction in the magnitude of a parameter, e.g. symptom, associated with the pathological condition being treated. As such, treatment also includes outcomes where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts are treatable according to the subject methods. Generally such hosts are mammals or mammalian, where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans. In other embodiment, the host will be an animal model for a human disease.

Of particular interest is treatment and prevention of diseases, conditions and disorders associated with abnormal expression of a cellular protein, usually present on the surface of a cell, e.g. a cancer cell.

The methods and compositions of the invention provide specific reagents that can be used in standard diagnostic procedures. For example, the antibodies or their immunoreactive fragments can be employed in immunoassays for detection of target antigens. To perform a diagnostic method, on of the compositions of the invention is provided as a reagent to detect a target antigen in a sample with which it reacts. Procedures for performing immunoassays are well established in the art and hence are not described here.

The human monoclonal antibodies generated by the subject methods may also be used for treatment or prevention of diseases and conditions. The monoclonal antibodies may be used to modulate the activities of target antigens that play a central role in disease development and/or progression. For example, a humanized anti-Her2 antibody, available commercially under the trademark HERCEPTIN®, which selectively inhibits growth of human breast cancer cells, is now employed as a potent drug to treat tens and thousands of breast cancer patients who overexpress the breast cancer antigen Her2.

Systems

Also provided by the subject invention are systems for practicing the subject methods, as described above. The subject systems at least include, for example, cells engineered to produce a fusogenic binding partner on their surface, and media (e.g. a PEG media) in which cell fusion takes place.

Kits

Also provided by the subject invention are kits for practicing the subject methods, as described above. The subject kits at least include one or more of: a cellular fusion partner containing a recombinant expression cassette for producing a fusogenic binding partner on its surface, a transgenic animal containing an expression cassette for producing a fusogenic binding partner on the surface of cells of the transgenic animal, a vector for expressing a fusogenic binding partner on the surface of a parental cell, and a bi-specific antibody for surface ligands on a parental pair of cells that can be fused.

Other optional components of the kit include: fusion partner cells, components for performing cell fusion, e.g., PEG, components for performing antibody binding assays, e.g., microtiter plates and ELISA reagents; buffers etc. The various components of the kit may be present in separate containers or certain compatible components may be precombined into a single container, as desired.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Also provided by the subject invention are kits including at least a computer readable medium including programming as discussed above and instructions. The instructions may include installation or setup directions. The instructions may include directions for use of the invention with options or combinations of options as described above. In certain embodiments, the instructions include both types of information.

Providing the software and instructions as a kit may serve a number of purposes. The combination may be packaged and purchased as a means for producing rabbit antibodies that are less immunogenic in a non-rabbit host than a parent antibody, or nucleotide sequences them.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

It is evident from the above results and discussion that the subject invention provides an important new means for generating hybrids cell. Specifically, the subject invention provides a method for generating hybrid cell, a composition of hybrid cells, methods for screening hybridoma cells and kits containing reagents and instructions for fusing cells. As such, the subject methods and systems find use in a variety of different applications, including research, therapeutic and other applications. Accordingly, the present invention represents a significant contribution to the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of fusing an antibody-producing cell with an immortal cell to produce a hybridoma cell, said method comprising:
    incubating an antibody-producing cell comprising a first partner of a binding partner pair on its surface with an immortal cell comprising a second partner of said binding partner pair on its surface under conditions sufficient for fusion of said cells, where said first partner or said second partner is an antibody of known specificity that is produced by a recombinant expression cassette in said cell, and wherein said antibody-producing cell also produces an antibody of unknown specificity, to produce said hybridoma cell.

2. The method of claim 1, wherein said antibody-producing cell and said immortal cell are cells selected from the group consisting of human, mouse, chicken, rat, and cow cells.

3. The method of claim 1, wherein said antibody-producing cell is a spleen cell.

4. The method of claim 3, wherein said antibody-producing cell is a rabbit spleen cell.

5. The method of claim 1, wherein the antibody of known specificity is produced transiently prior to incubating the cells for fusion.

6. The method of claim 1, wherein said hybridoma cell produced by said method is a hybridoma cell producing a monoclonal antibody.

7. The method of claim 1, wherein said antibody of known specificity is selected from the group consisting of a bivalent antibody and a modified antibody.

8. A composition comprising:
   a) a plurality of antibody producing cells that secrete antibodies of unknown specificity and comprising a first partner of a binding partner pair on their surfaces;
   b) a plurality of immortal cells comprising a second partner of said binding partner pair on their surfaces; and
   c) at least one hybrid cell, wherein said hybrid cell is a hybrid of said antibody-secreting cells and said immortal cells;
       wherein one of said partners of said binding partner pair comprises a cell surface recombinant antibody of known specificity.

9. A composition comprising:
   a hybrid cell, wherein said hybrid cell comprises an exogenous fusogenic binding partner pair on its surface, wherein one of said partner of said fusogenic binding partner pair comprises a recombinant antibody of know specificity, and wherein said hybrid cell also secretes an antibody of unknown specificity.

10. A method of screening for a monoclonal antibody of interest, said method comprising:
    incubating a first cell comprising a first partner of a binding partner pair on its surface with a second cell comprising a second partner of said binding partner pair on its surface under conditions sufficient for fusion of said cells to produce at least one hybrid cell, wherein one of said partners of said binding partner pair comprises a recombinant antibody of known specificity; and
    screening antibodies secreted by said hybrid cell to determine whether said hybrid produces a monoclonal antibody of interest.

11. The method of claim 10, wherein said screening step is screening for binding specificity of said monoclonal antibody of interest to an antigen.

12. The method of claim 10, wherein said screening step is screening for binding specificity to an epitope of said antigen.

13. The method of claim 10, wherein said screening step is screening for a therapeutic antibody.

14. The method of claim 10, wherein said screening step is screening for an inhibitory monoclonal antibody that inhibits an interaction between a first biopolymeric compound and a second biopolymeric compound.

15. The method of claim 10, wherein said screening step is screening for an inhibitory monoclonal antibody that inhibits an enzymatic reaction.

16. A method of producing a monoclonal antibody of interest, said method comprising:
    (a) performing the method of claim 10; and
    (b) purifying a monoclonal antibody of interest.

17. A kit comprising:
    (a) nucleic acids encoding at least two partners of a fusogenic binding partner pair, wherein one of said partners of said fusogenic binding partner pair comprises a recombinant antibody;
    (b) instructions for using said nucleic acids in a method of fusing two cells.

18. The kit of claim 17, further comprising at least one parental cell.

19. The kit of claim 18, wherein said nucleic acid is contained within said at least one parental cell.

20. The kit of claim 17, wherein said nucleic acids comprised within a plasmid vector.

21. A system comprising:
    (a) a first plurality of cells engineered to produce a first binding partner of a fusogenic binding partner pair on their surfaces;
    (b) a second plurality of cells engineered to produce a second binding partner of said fusogenic binding partner pair on their surfaces; and
    (c) media in which cell fusion takes place,
        wherein one of said binding partners of said fusogenic binding partner pair comprises a recombinant antibody of known specificity.

22. The system of claim 21, wherein said media contains polyethylene glycol.

* * * * *